(12) United States Patent
Stoller et al.

(10) Patent No.: US 10,104,883 B2
(45) Date of Patent: Oct. 23, 2018

(54) NON-AQUEOUS SOLUTION OF PLANT-GROWTH REGULATOR(S) AND POLAR AND/OR SEMI-POLAR ORGANIC SOLVENT(S)

(71) Applicant: Stoller Enterprises, Inc., Houston, TX (US)

(72) Inventors: Jerry Stoller, Houston, TX (US); Ritesh Sheth, Friendswood, TX (US)

(73) Assignee: Stoller Enterprises, Inc., Houston, TX (US)

( * ) Notice: Subject to any disclaimer, the term of this patent is extended or adjusted under 35 U.S.C. 154(b) by 0 days.

(21) Appl. No.: 14/995,434

(22) Filed: Jan. 14, 2016

(65) Prior Publication Data

US 2016/0198714 A1    Jul. 14, 2016

Related U.S. Application Data

(60) Provisional application No. 62/103,410, filed on Jan. 14, 2015.

(51) Int. Cl.
*A01N 25/02*    (2006.01)

(52) U.S. Cl.
CPC .................. *A01N 25/02* (2013.01)

(58) Field of Classification Search
CPC ........ A01N 25/02; A01N 37/10; A01N 39/02; A01N 43/38; A01N 43/90; A01N 45/00

USPC .......................................................... 504/136
See application file for complete search history.

(56) References Cited

U.S. PATENT DOCUMENTS

| 4,769,061 A | * | 9/1988 | Comai | C12N 15/8275 |
| | | | | 435/193 |
| 6,071,857 A | * | 6/2000 | Vogt | A01N 25/02 |
| | | | | 424/405 |
| 9,326,452 B2 | * | 5/2016 | Liptay | A01G 1/001 |
| 2003/0013610 A1 | * | 1/2003 | Killick | A01N 43/90 |
| | | | | 504/320 |
| 2005/0288188 A1 | | 12/2005 | Volgas | |
| 2008/0039322 A1 | * | 2/2008 | Wang | A01N 25/02 |
| | | | | 504/136 |
| 2011/0021353 A1 | | 1/2011 | Doolittle, Jr. | |
| 2015/0080216 A1 | * | 3/2015 | Wikeley | A01N 43/08 |
| | | | | 504/136 |
| 2015/0173365 A1 | * | 6/2015 | Devisetty | A01N 43/12 |
| | | | | 504/297 |

FOREIGN PATENT DOCUMENTS

FR    2999385 A1 *  6/2014  ............. A01N 25/02

* cited by examiner

*Primary Examiner* — Sreenivasan Padmanabhan
*Assistant Examiner* — Courtney A Brown
(74) *Attorney, Agent, or Firm* — Yancy IP Law, PLLC

(57) ABSTRACT

The present invention generally relates to non-aqueous solutions of plant growth regulator(s) and polar and/or semi-polar organic solvent(s), methods for making said non-aqueous solution, and methods for improving the growth and crop productivity of plants using said non-aqueous solution.

20 Claims, No Drawings

NON-AQUEOUS SOLUTION OF PLANT-GROWTH REGULATOR(S) AND POLAR AND/OR SEMI-POLAR ORGANIC SOLVENT(S)

CROSS-REFERENCE TO RELATED APPLICATIONS

This application claims the benefit, under 35 U.S.C. 119(e), of U.S. Provisional Application No. 62/103,410 filed Jan. 14, 2015, the contents of which are incorporated herein by reference.

BACKGROUND OF THE INVENTION

1. Field of the Invention

The present invention generally relates to non-aqueous solutions of plant growth regulator(s) and polar and/or semi-polar organic solvent(s), methods for making said non-aqueous solution, and methods for improving the growth and crop productivity of plants using said non-aqueous solution.

2. Description of the Background

As provided in International Publication No. WO 2012068473, the contents of which are expressly incorporated herein by reference, plant growth and development as well as productivity (e.g., crops, seeds, fruits etc.) are known to be regulated by growth factors, mineral components and small molecules that signal for the expression of genes that enhance the level of plant productivity, whether in quantity or quality. Traditional approaches for improving plant productivity have included the application of various minerals and nitrogen components as necessary additions or substrates to crop plant or other plant productivity. However, such approaches have tended to knowingly, or unknowingly, disregard the growth factors (e.g., phytohormones and/or other small molecules) required for enhanced productivity.

Traditionally, mineral fertilizers have been predominately applied to growing crop plants. Difficulties arise, however, when external stresses impede successful plant development, especially of grain or seed crops and/or other crops. Physical stresses, such as those inflicted by environmental temperatures being either too low or too high, and in particular high temperatures, are especially problematic. Moreover, the state-of-the-art agronomic practice does not employ plant growth regulators to overcome a plant's difficulty, due to such stresses, in producing sufficient amounts of nutrients, e.g., sugars, to prevent autophagy (i.e., cannibalization of previously-formed plant cells by newly-forming cells to compensate for a dearth of cell nutrients). It is well known that mineral fertilizers provide eighteen minerals that are necessary for crop growth and development. Signaling molecules, such as plant growth regulators or other molecules, are known to enhance crop productivity through the expression of certain genes. Furthermore, much research has been conducted into the use of plant growth regulators and their effects on plant growth and development.

An alternative, more natural approach, which is becoming ever more appreciated, is based upon the theory that plants already have the necessary genes/genetic code to produce greater quantities and/or qualities of various plant tissues as well as to thrive in the face of common adversities, such as drought, disease, and insect infestations. But, to realize the full expression of this innate genetic material and the plant's full potential, the plant must receive various naturally-occurring nutrients and/or phytohormones in specific concentrations, at specific times during the plant's growth, and to specific parts or tissues of the plant.

As provided in International Publication No. WO 2005/021715, the contents of which are expressly incorporated herein by reference, plant hormones have been known and studied for years. Plant hormones may be assigned to one of a few categories: auxins, cytokinins, gibberellins, abscisic acid, brassinosteroids, jasmonates, salicylic acids, polyamines, peptides, nitric oxides, strigolactones and ethylene. Ethylene has long been associated with fruit ripening and leaf abscission. Abscisic acid causes the formation of winter buds, triggers seed dormancy, controls the opening and closing of stomata and induces leaf senescence. Gibberellins, primarily gibberellic acid, are involved in breaking dormancy in seeds and in the stimulation of cell elongation in stems. Gibberellins are also known to cause dwarf plants to elongate to normal size. Cytokinins, are produced primarily in the roots of plants. Cytokinins stimulate growth of lateral buds lower on the stem, promote cell division and leaf expansion and retard plant aging. Cytokinins also enhance auxin levels by creating new growth from meristematic tissues in which auxins are synthesized. Auxins, promote both cell division and cell elongation, and maintain apical dominance. Auxins also stimulate secondary growth in the vascular cambium, induce the formation of adventitious roots and promote fruit growth.

The most common naturally occurring auxin is indole-3-acetic acid (IAA). However, synthetic auxins, including indole-3-butyric acid (IBA); naphthalene acetic acid (NAA); 2,4-dichlorophenoxy acetic acid (2,4-D); and 2,4,5-trichlorophenoxy acetic acid (2,4, 5-T or Agent Orange) are known. While these are recognized as synthetic auxins, it should be acknowledged that IBA does naturally occur in plant tissues. Many of these synthetic auxins have been employed for decades as herbicides, producing accelerated and exaggerated plant growth followed by plant death. Agent Orange gained widespread recognition when it was used extensively by the United States Army and Air Force in defoliation applications during the Vietnam War. 2, 4-D finds continuing use in a number of commercial herbicides sold for use in agriculture, right of way, and turf and ornamental markets.

Agriculturally, active ingredients are often provided in the form of concentrates suitable for dilution with water. Many forms of agricultural concentrates are known and these consist of the active ingredient and a carrier, which can include various components. Water-based concentrates are obtained by dissolving, emulsifying and/or suspending agriculturally active technical materials in water. Due to the relatively complex supply chain for crop protection agents, such concentrate formulations can be stored for long periods and may be subjected during storage and shipping to extreme temperature variations, high-shear and repetitive vibration patterns. Such supply chain conditions can increase the likelihood of formulation failure due to, for example, water mediated degradation and stability problems.

Accordingly, the efficient use of aqueous systems with certain agrochemicals and crop protection agents is restricted due to their poor chemical stability when exposed to water during storage. Typically, hydrolysis is the most common water-mediated degradation mechanism; however, agricultural concentrates with water-sensitive active ingredients are also subject to oxidation, dehalogenation, bond cleavage, Beckmann rearrangement and other forms of degradation on exposure to water.

In some cases it may be desirable to combine different agrochemicals to provide a single formulation taking advantage of the additive properties of each separate agrochemical and optionally an adjuvant or combination of adjuvants that provide optimum biological performance. For example, transportation and storage costs can be minimized by using a formulation in which the concentration of the active agrochemical(s) is as high as is practicable and in which any desired adjuvants are "built-in" to the formulation as opposed to being separately mixed inside the spray tank. The higher the concentration of the active agrochemical(s) however, the greater is the probability that the stability of the formulation may be disturbed, or that one or more components may phase separate.

Another challenge arises where a user of an agrochemical liquid concentrate formulation dilutes the formulation in water (for example in a spray tank) to form a dilute aqueous spray composition. Such agrochemical spray compositions are widely used, but their performance sometimes can be limited by the tendency for certain agrochemicals to degrade in a spray tank on exposure to water. For example, agrochemical breakdown can increase with increasing alkalinity and water temperature, and with the length of time the spray composition is left in the tank.

Considering the variety of conditions and special situations under which agrochemical liquid concentrate formulation are stored, shipped and used around the world, there remains a need for concentrate formulations of agrochemicals, including water sensitive agrochemicals that provide stability benefits under at least some of those conditions and situations. There is a further need for such formulations having high loading that are stable before being diluted with water under a wide range of field conditions.

US 20120045497 documents the stabilizing of liquid agrochemical compositions which comprise flowable, non-aqueous dispersion concentrates comprising a continuous substantially water-miscible liquid phase, a dispersed water-immiscible liquid phase, and a colloidal solid.

Furthermore, it is known that gibberellins and abscisic acid cannot be directly applied to a crop and require a solvent system as a carrier for such applications. Since gibberellins are slowly hydrolyzed in aqueous solutions, they cannot be stored long term in aqueous solutions. Commercial solutions are thus non-aqueous. Gibberellins are known to be dissolved in methanol. Methanol is both flammable and poisonous. The Dangerous Goods Regulations (DGR) therefore demand that all products which contain methanol, including gibberellin solutions, be marked as both flammable and poisonous and handled accordingly which has led to increased restrictions in some states and countries. Accordingly, US 20030013610 proposes the use of a lipophilic solvent system. It has been found that the lack of solubility of gibberellins in lipophilic solvents has been overcome through the use of certain lipophilic solvent systems. This is of interest because they are not flammable like methanol. Such systems include a plant growth promoter composition comprising: (a) not in excess of 20% by weight of one or more gibberellins; and (b) an essentially non-aqueous solvent system comprising: (i) 30 to 99% by weight of one or more lipophilic solvents; (ii) at least an equivalent molar amount to the gibberellin(s) of one or more lipophilic alkaline coupling agents which enable the gibberellin(s) to form a lipophilic solvent soluble complex; (iii) 1 to 50% by weight of one or more emulsifiers which blend with the lipophilic solvent(s) to form a homogeneous product and enable dispersion of the composition into water for application; and (iv) optionally, not in excess of 15% by weight of one or more viscosity reducing co-solvents.

SUMMARY OF THE INVENTION

The present invention is directed to a non-aqueous solution of: 1) at least one plant growth regulator and 2) at least one polar organic solvent and/or at least one semi-polar organic solvent. The present invention further includes methods for making said non-aqueous solution, and methods for improving the growth and crop productivity of plants using said non-aqueous solution. A polar organic solvent is defined as that which dissolves ionic and other polar solutes. Semi-polar organic solvents induce a certain degree of polarity in non-polar molecules. A measurement of polarity may be determined by its dielectric constant. Semi-polar organic solvents and polar organic solvents defined in this invention are those organic solvents that have dielectric constants greater than 10 @ 20° C. For example, polar organic solvents may include, but are not limited to alcohols, dialkyl ketones, alkylene carbonates, alkyl esters, and aryl esters. For example, semi-polar organic solvents may include, but are not limited to polyethylene glycols of various molecular weights. The present invention includes methods by which plant growth can be manipulated through the addition of said non-aqueous solution by application to roots or aerial tissues.

The present invention is directed to methods for improving the growth and crop productivity of plants by introducing plant growth regulators, such as phytohormones, to the tissue of the plant using polar and semi-polar organic solvent(s). In the methods of the present invention, a plant hormone in an amount effective to produce the desired effect, e.g., improved growth, improved fruit set, or improved plant architecture, is dissolved in polar and semi-polar organic solvent(s) and applied as an aqueous solution to the plant tissue.

The non-aqueous solution containing plant growth regulators has enhanced stability compared to aqueous composition by the use of the polar and semi-polar organic solvent(s). This improved stability of the non-aqueous solution preserves more biochemical activity compared to the traditional aqueous compositions. This improves plant architecture by producing a stockier, more compact plant characterized by increased branching, shorter stem internodes, prolific root development and thicker leaves with enhanced photosynthetic capacity and sugar production. This architectural change increases photosynthate storage capacity; flowering points; fruit initiation, sizing and retention; and ultimately yield.

DETAILED DESCRIPTION OF THE INVENTION

The non-aqueous solution of the present invention includes: 1) at least one plant growth regulator, also referred to herein as PGR, and 2) at least one polar organic solvent and/or at least one semi-polar organic solvents. Herein are also disclosed methods for making said non-aqueous solution and methods for improving the growth and crop productivity of plants using said non-aqueous solution. The present invention includes methods by which plant growth can be manipulated through the addition of said non-aqueous solution by application to plant tissue.

As provided herein, it is understood that the term "non-aqueous" may include small amounts of water, preferably less than 5 wt. %, preferably less than 4 wt. %, preferably less than 3 wt. %, preferably less than 2 wt. %, preferably less than 1 wt. %, and preferably less than 0.5 wt. %. However, it is preferred that water is not intentionally added to the present non-aqueous solution.

Plant Growth Regulators/Phytohormones

While the plant growth regulators (PGRs) provided in the non-aqueous solution may be any effective plant hormones, the phytohormone is typically selected from ethylene, auxins, cytokinins, gibberellins, abscisic acid, brassinosteroids, jasmonates, salicylic acids, peptides, polyamines, nitric oxide, strigolactones, precursors, derivatives and mixtures thereof.

The auxin is preferably selected from the group consisting of the natural auxins, synthetic auxins, auxin metabolites, auxin precursors, auxin derivatives and mixtures thereof. The preferred auxin is a natural auxin, most preferably indole-3-acetic acid. The presently preferred synthetic auxin is indole-3-butyric acid (IBA). Other exemplary synthetic auxins which may be employed in the present invention include indole 3-propionic acid, indole-3-butyric acid, phenylacetic acid, naphthalene acetic acid (NAA), 2,4-dichlorophenoxy acetic acid, 4-chloroindole-3-acetic acid, 2,4,5-trichlorophenoxy acetic acid, 2-methyl-4-chlorophenoxy acetic acid, 2,3,6-trichlorobenzoic acid, 2,4,6-trichlorobenzoic acid, 4-amino-3,4,5-trichloropicolinic acid and mixtures thereof.

The cytokinin is preferably selected from one or more of the following: zeatin, various forms of zeatin, N6-benzyl adenine, N6-(delta-2-isopentyl) adenine, 1,3-diphenyl urea, thidiazuron, CPPU (forchlorfenuron), kinetin or other chemical formulations with cytokinin activity. The preferred cytokinin is kinetin.

The gibberellin is preferably selected from one or more of the following: GAi, GA2, $GA_3$, GA4, GA5, GA6, GA7, $GA_8$, GA9, GA10, GA11, $GA,_2$, $GA,_3$, $GA,_4$, $GA,_5$, $GA_{16}$, $GA_{17}$, $GA,_8$, $GA_{19}$, $GA_{20}$, $GA_2i$, $GA_{22}$, $GA_{23}$, $GA_{24}$, $GA_{25}$, $GA_{26}$, $GA_{27}$, $GA_{28}$, $GA_{29}$, $GA_{30}$, $GA_{31}$, $GA_{32}$, $GA_{33}$, $GA_{34}$, $GA_{35}$, $GA_{36}$, $GA_{37}$, $GA_{38}$, $GA_{39}$, $GA_{40}$, $GA_{41}$, $GA_{42}$, $GA_{43}$, $GA_{44}$, $GA_{45}$, $GA_{45}$, $GA_{47}$, GA48, $GA_{49}$, GAso, $GA_{51}$, $GA_{52}$, $GA_{53}$, $GA_{54}$, $GA_{55}$, $GA_{56}$, $GA_{57}$, $GA_{58}$, $GA_{59}$, $GA_{60}$, $GA_{61}$, $GA_{62}$, $GA_{63}$, $GA_{64}$, $GA_6 5$, $GA_6 6$, $GA_{67}$, $GA_{68}$, $GA_{69}$, $GA_{70}$, GA71, $GA_{72}$, $GA_{73}$, $GA_{74}$, $GA_{75}$, $GA_{76}$, $GA_{77}$, $GA_{78}$, $GA_{79}$, $GA_{80}$, $GA_8i$, $GA_{82}$, $GA_{83}$, $GA_8$, $GA_{85}$, $GA_{86}$, $GA_{87}$, $GA_{88}$, $GA_{89}$, $GA_{90}$, $GA_9i$, $GA_{92}$, $GA_{93}$, $GA_{94}$, $GA_{95}$, $GA_{96}$, $GA_{97}$, $GA_{98}$, $GA^{\char`\^}$, GA100, GA101, $GA_{)02}$, $GAio_3$, GA104, GA105, GA106, $GAio_7$, GAios, $GAi_{09}$, GAno, GAm, $GAn_2$, GA113, GAl $i_4$, GA115, GA116, GAi i7, GAi is, $GAn_9$, GAno, $GAi_2i$, $GAi_{22}$, $GAi_{23}$, $GAi_{24}$, $GAi_{25}$, and/or GAi26. The preferred gibberellin is the gibberellic acid, $GA_3$.

The auxins, preferably indole-3-butyric acid (IBA), are present in the non-aqueous solution in an amount such that the auxin is between about 0.001 to 10 wt. %, preferably between about 0.005 to about 5 wt. %, preferably between 0.005 to about 2 wt. %, preferably between 0.005 to about 1 wt. %, preferably between 0.005 to about 0.5 wt. %, preferably between 0.005 to about 0.85 wt. %, and preferably between about 0.005 to about 0.05 wt. % of the non-aqueous solution.

The gibberellin, preferably gibberellic acid ($GA_3$), are present in the non-aqueous solution in an amount such that the gibberellin is between about 0.001 to 20 wt. %, preferably between about 0.001 to 15 wt. %, preferably between about 0.001 to 7.5 wt. %, preferably between 0.005 to about 5 wt. %, preferably between about 0.005 to about 1 wt. %, preferably between about 0.005 to about 0.11 wt. %, preferably between about 0.005 to about 0.07 wt. %, and preferably between about 0.005 to about 0.05 wt. % of the non-aqueous solution.

The cytokinin, preferably kinetin, are present in the non-aqueous solution in an amount such that the cytokinin is between about 0.003 to 0.3 wt. %, preferably between 0.009 to 0.15 wt. %, preferably between about 0.0015 to 0.15 wt. %, and most preferably between about 0.01 to 0.05 wt. % of the non-aqueous solution.

As provided in International Publication WO 2012068473, the contents of which are expressly incorporated herein by reference, in a preferred embodiment of the present invention, the plant growth regulator are included as a PGR mixture of two plant hormones—cytokinin and gibberellin. When used together, the ratio of the plant growth regulators, cytokinin and gibberellin, preferably ranges from 1:10 to 1:300 and more preferably from 1:20 to 1:40. A ratio of approximately 1:30 is most preferable. Nonetheless, to obtain the best results, the absolute amount of the cytokinins and gibberellins must vary proportionally to the volume/weight of the treated plants and their fruit.

Additionally, in a preferred embodiment of the present invention, the plant growth regulator may include a PGR mixture of the following two phytohormones: cytokinin and auxin. When used together, the ratio of the plant growth regulators, cytokinin and auxin, preferably ranges from 1:10 to 1:300 and more preferably from 1:20 to 1:40. A ratio of approximately 1:30 is most preferable. Nonetheless, to obtain the best results, the absolute amount of the cytokinins and gibberellins must vary proportionally to the volume/weight of the treated plants and their fruit.

Additionally, in a preferred embodiment of the present invention, the plant growth regulator may include a PGR mixture of three plant hormones—cytokinin, gibberellin, and auxin. In a preferred mixture, the cytokinin is kinetin, the gibberellin is GA3, and the auxin is IBA. When used together, the amount of kinetin is preferably 4-6 times, and more preferably 2-3 times more than the amount of gibberellic acid and the amount of IBA is preferably 1-1.5 times more than the amount of gibberellic acid. The non-aqueous solution may preferably include: a) 0.2-0.005 wt. %, more preferably 0.10-0.009 wt. % kinetin; b) 0.1-0.003 wt. %, more preferably 0.05-0.005 wt. % GA3; and c) 0.1-0.003 wt. %, more preferably 0.05-0.005 wt. % IBA.

Polar and Semi-polar Organic Solvent

A wide variety of polar and semi-polar organic solvents may be used, including the polar and semi-polar organic solvents ethanol, n-propanol, iso-propanol, ethyl lactate, 3-hydroxybutyrate (ethyl and propyl esters), glycols, glycerols, polyethylene glycol, polypropylene glycol, propylene carbonate and combinations thereof. Most preferably, propylene glycol is used as the organic solvent in the non-aqueous solution of the present invention. In one embodiment of the present invention, the polar and semi-polar organic solvent is a single or combination of "non-volatile, polar or semi-polar organic solvents", herein defined to exclude those volatile organic compounds (VOCs) with a vapor pressure less than 0.1 mm Hg at 20° C.

Additional Ingredients Includes/Excluded

A preferred embodiment of the present invention includes the addition of surfactants, antifoams, and/or preservatives known to those of skill in the art. The surfactant may include, but are not limited to, the group consisting of carboxylates, sulfonates, natural oils, alkylamides, arylamides, alkylphenols, arylphenols, ethoxylated alcohols, polyethylene, carboxylic esters, polyalkylglycol esters, anhydrosorbitols, glycol esters, carboxylic amides, monoalkanolamine, polethylene fatty acid amides, polysorbates, cyclodextrins, sugar based, silicone based, polyalkylated alcohols, and alkylaryl ethoxylates. In a preferred embodiment, the non-aqueous solution consists of only the plant growth regulator(s), optional mineral(s), surfactant, and the polar and semi-polar organic solvent(s) and any impurities inherent therein.

In an alternate preferred embodiment, the non-aqueous solution only includes one solvent, that is, the polar and semi-polar organic solvent. As previously indicated this non-aqueous solution may include small amounts of water, preferably less than 5 wt. %, more preferably less than 1 wt. %, and most preferably less than 0.5 wt. %. Most preferably, the non-aqueous solution only includes one solvent, that is, the polar and semi-polar organic solvent with no intentional addition of water. As previously indicated, the non-aqueous solution may further include a minerals selected from the group consisting of the alkaline earth metals, transition metals, boron and mixtures thereof. Such minerals preferably are selected from the group consisting of calcium, magnesium, zinc, copper, manganese, boron, iron, cobalt, molybdenum and mixtures thereof. When included, the minerals may be present in the range from about 0.001 to about 10.0 wt. %, preferably from about 0.001 to about 3.0 wt. %. The non-aqueous solution optionally, but preferably, includes one or more minerals that assist in the uptake of the plant growth regulator(s) by plant tissues and/or compliment the utilization of the plant hormones by the plant tissues. Preferred minerals include zinc, nitrogen, potassium, calcium and boron, with nitrogen, potassium, calcium and/or boron. In a preferred embodiment, the metals include, but are not limited to, metal chlorides, metal sulfates, sodium or potassium salts of and chelated metals. Specific examples include, but are not limited to metal chlorides, metal sulfates, EDTA chelated metals, and other suitable metal compounds.

The non-aqueous solution may be combined with a nitrogen-containing fertilizer, such as a liquid nitrogen fertilizer comprising approximately one-half urea and one-half ammonium nitrate. Such a liquid nitrogen fertilizer has a nitrogen content of about 28 to 32 percent. Preferably, the liquid nitrogen fertilizer is blended with the non-aqueous solution containing the plant growth regulator(s) and other minerals, if any, just prior to application, such that only a single field application of the solution/fertilizer is needed, thereby reducing labor and equipment costs that would otherwise be required due to a later nitrogen-only field application.

Method of Making

The non-aqueous solution is generally produced by dissolving at least one plant growth regulator in at least one polar and semi-polar organic solvent and either mixing at room temperature or at a temperature up to the boiling point of the polar and semi-polar organic solvent, more preferably below 120° C. and most preferably below 100° C. It is believed that heating the hormones in the polar and/or semi-polar organic solvent up to 120° C. will not significantly degrade the plant growth regulators.

Application to Plants

In a preferred embodiment, the non-aqueous solution is combined with water prior to application to the plant (e.g. within a few hours of application to the plant) to provide a water-diluted composition. The amount of water added to the non-aqueous solution depends on the required concentration of the active ingredients needed to regulate plant growth as known to those of skill in the art.

In a more preferred embodiment of the methods of the present invention, a water-diluted composition of the non-aqueous solution of the plant growth regulator is applied to the roots, foliage, flowers or fruits of a plant after planting. While application to the roots or tubers prior to planting or by soil application after planting, may produce the best results in some circumstances, in others, application to the foliage may be preferred. The specific crop and the desired result must be taken into account when selecting an application method. The non-aqueous solution and/or water-diluted composition including the non-aqueous solution may be applied using conventional irrigation or spray equipment.

The method preferably includes the application of the non-aqueous solution of plant growth regulators, such as a cytokinin, to the foliage and/or flowers of plants at or about the time of the beginning of plant flowering (e.g., during meiosis and when pollen is about to enter dehiscence). The non-aqueous solution may be applied to the soil in any appropriate fashion, such as, for example, in an opened furrow near the plant roots, which furrow may subsequently be closed. It may also be applied with various forms of irrigation, such as overhead or drip tape, or furrow irrigation, among others. Application of agricultural chemicals may be accomplished in any of several ways well known to those skilled in the art, including but not limited to, foliar applications, soil applications, irrigation applications, etc. In a preferred method of the invention, the non-aqueous solution is readied and applied to the roots of growing plants, or via the soil in which the plants are growing, through drip irrigation. Other fertigation-type application methods that may be employed include, but are not limited to, broadcasting (e.g. conventional irrigation) and other types of placement application (e.g. side dressing; microjets, etc.). Broadcast application is an acceptable method, if sufficient irrigation is permitted to wash the non-aqueous solution from the foliage and above-ground tissues of the plants and into the soil/roots.

The present invention includes seeds, seed pieces, dry fertilizer, talc, gypsum or tubers for producing plants having dispersed on the surface thereof a phytohormone, e.g., an auxin or other PGR, in an amount effective to alter plant architecture as explained above, but in an amount insufficient to negatively affect growth of the plant tissues. When applied as a non-aqueous solution, the non-aqueous solution containing the plant growth regulator, e.g., an auxin or another PGR, may be sprayed on seeds or tubers using conventional spray equipment. Alternatively, the seeds, fertilizer, talc, gypsum or tubers may be immersed in a non-aqueous solution of the plant growth regulator. Seeds, fertilizers, talc, gypsum or tubers may be treated prior to planting by spraying with or by immersion in such non-aqueous solutions.

The preferred method of applying PGRs may be along with a boron-containing solution. Boron will stabilize the auxin in plant tissues to which such solutions are applied.

The application of a metal or metalloid, preferably boron, together with the PGR extends the effective life of the PGR, thus permitting longer times between repeat applications. Additionally, boron has been reported to have insecticidal, fungicidal and bacteriocidal activities. Accordingly, it is believed that application of PGRs, together with boron, will improve the effect of the PGR in suppressing insect and pathogen infestation in plants.

Preferably, but optionally, a low concentration of potassium is also applied together with the plant growth regulator to enhance the effects of the plant hormone. Potassium, if applied with the cytokinin, is preferably applied at very low concentrations between about ¼ lb. to about 2 lbs. per acre, more preferably between about ½ lb. to about 1½ lbs. per acre, and most preferably about 1 lb. per acre.

While the methods of the present invention may be used with substantially all plants, they are particularly useful when applied to crop plants, e.g., dry beans, soy beans, onions, cucumbers, tomatoes, potatoes, corn, cotton, canola, wheat and the like.

In a first step of applying the non-aqueous solution to the plants, the plant hormone is readied for application to the plants to be treated. The plant hormone is preferably applied to the plants in a non-aqueous solution. Therefore, readying the plant hormone may include one or more of the following activities: diluting the non-aqueous solution of the plant hormone with sufficient amounts of solvent to create the desired concentration of plant hormone, adding low concentrations of minerals and/or other fertilizers to the diluted solution to enhance the effects of the applied plant hormone, loading the non-aqueous solution of the plant hormone (with or without minerals and/or fertilizers) into a sprayer or tank for subsequent application to the plants to be treated, calibrating the sprayer or dosing applicator to meter the desired amount of the solution of the plant hormone to the plants to be treated and transporting the solution of the plant hormone (with or without minerals and/or fertilizers) the location of the plants to be treated.

As provided in International Publication No. WO 2005/021715, the contents of which are expressly incorporated herein by reference, auxin level may be manipulated within a desired range by application of a plant growth regulator or phytohormone, e.g., cytokinin or gibberellic acid.

International Publication No. WO 2012135366 and US Publication No. US20120295788, the contents of which are expressly incorporated herein by reference, teach exogenous application to the plant canopy (i.e. leaves and flowers) of the plant growth regulator/phytohormone cytokinin. Additionally, the application of low concentrations of potassium along with the cytokinin has been found to substantially increase the effect of the cytokinin.

EXAMPLES

Tables 2-4 and 6-8 shows Stability Studies for kinetin, IBA, and GA3 in the products identified in further detail below. The EPA Guidelines on Stability that issued on Nov. 16, 2012 to the Office of Pesticide Programs (OPP) relating to "Accelerated Storage Stability and Corrosion Characteristics Study Protocol" were followed. As provided in the EPA Guidelines, accelerated storage stability can be used to fulfill EPA data requirements. OPP has determined that this study, conducted for 14 days at an elevated temperature (54° C.), provides adequate data in certain circumstances to allow EPA to make a regulatory finding regarding the stability of the product and the effect of the formulation on the product packaging.

The products evaluated in the Accelerated Storage Stability Testing include the Active Ingredients is supplied in Tables 1 and 5 below. Table 5 lists the active ingredient in a non-aqueous solution of propylene glycol as the solvent, which contains less than 0.5 wt. % water, in accordance with the present invention. The stability data compares the non-aqueous solution of the plant hormones in accordance with the present invention (referred to in this Example as "Organic"). Specifically, the non-aqueous solutions were formulated with propylene glycol as the solvent instead of water with less than 0.5% water in the solution. Propylene glycol is an acceptable solvent since it is considered a low Volatile Organic Compound (VOC) in some areas. A low VOC is defined in this invention as a compound with a vapor pressure less than 0.1 mm Hg at 20° C. The vapor pressure of propylene glycol is 0.08 mm Hg at 20° C. As can be seen in the Tables, the plant hormones retained their stability the best in the Organic, i.e. non-aqueous solutions, formulated with propylene glycol as the solvent in accordance with the present invention. Tables 2 and 6 show the stability of Kinetin in the various compositions at 0, 7 and 14 days. Tables 3 and 7 show the stability of IBA in the various compositions at 0, 7 and 14 days. Tables 4 and 8 show the stability of GA3 in the various compositions at 0, 7, and 14 days.

TABLE 1

|  | Kinetin | | | IBA | | | GA$_3$ | | |
| --- | --- | --- | --- | --- | --- | --- | --- | --- | --- |
|  | Label | EPA Label (max) | EPA Label (min) | Label | EPA Label (max) | EPA Label (min) | Label | EPA Label (max) | EPA Label (min) |
| #1 | 0.090% | 0.099% | 0.081% | 0.050% | 0.0550% | 0.0450% | 0.050% | 0.0550% | 0.0450% |
| #2 | 0.009% | 0.010% | 0.008% | 0.005% | 0.0055% | 0.0045% | 0.005% | 0.0055% | 0.0045% |
| #3 | 0.15% | 0.165% | 0.135% | 0.85% | 0.9350% | 0.7650% |  |  |  |
| #4 (Aq) | 0.09% |  |  | 0.045% |  |  | 0.03% |  |  |
| #5 (Aq) | 0.09% |  |  | 0.050% |  |  | 0.05% |  |  |

The product's provided in Table 1 correspond to the following labels indicated below:
1 - Plant Growth Regulators 10X
2 - Plant Growth Regulators 1X
3 - Plant Growth Regulator
4 - Competitors (Aqueous)
5 - Plant Growth Regulator 1X (Aqueous)

TABLE 2

Kinetin Stability data

|    | 0 days | 7 days | 14 days |
|----|--------|--------|---------|
| #1 | 100.0% | 98.0%  | 96.9%   |
| #2 | 100.0% | 109.1% | 100.0%  |
| #3 | 100.0% | 102.9% | 100.7%  |
| #4 | 100.0% | 17.2%  | 16.2%   |
| #5 | 100.0% | 83.2%  | 68.9%   |

TABLE 3

IBA Stability data

|    | 0 days | 7 days | 14 days |
|----|--------|--------|---------|
| #1 | 100.0% | 91.7%  | 89.6%   |
| #2 | 100.0% | 98.0%  | 98.0%   |
| #3 | 100.0% | 98.7%  | 100.0%  |
| #4 | 73.1%  | 64.9%  | 61.6%   |
| #5 | 100.0% | 94.0%  | 89.4%   |

TABLE 4

GA3 Stability data

|    | 0 days | 7 days | 14 days |
|----|--------|--------|---------|
| #1 | 100.0% | 92.3%  | 88.7%   |
| #2 | 100.0% | 95.9%  | 95.9%   |
| #4 | 100.0% | 1.3%   | 1.3%    |
| #5 | 100.0% | 0.0%   | 0.0%    |

TABLE 5

|     | Kinetin | IBA   | $GA_3$ | Solvent (Polar/Semi-Polar) | Mineral |
|-----|---------|-------|--------|----------------------------|---------|
| #6  | 0.095   | 0.047 | 0.11   | Polyethylene Glycol 200    | None    |
| #7  | 0.095   | 0.047 | 0.07   | Polyethylene Glycol 400    | None    |
| #8  | 0.090   | 0.05  | 0.05   | Isopropanol                | None    |
| #9  | 0.100   | 0     | 0      | Ethyl Lactate/Glycerol     | None    |
| #10 | 0       | 0     | 7.5    | Propylene Glycol           | None    |
| #11 | 0       | 0     | 15     | Propylene Glycol           | None    |
| #12 | 0       | 0     | 20     | Propylene Glycol           | None    |
| #13 | 0.085   | 0.04  | 0.065  | Propylene Glycol           | 1.2% $MnCl_2$ |
| #14 | 0.09    | 0.04  | 0.07   | Propylene Glycol           | 5% BMZ  |
| #15 | 0.085   | 0.04  | 0.055  | Propylene Glycol           | 2.5% BMZ |

*BMZ = Stoller Mixrite BMZ: 0.9% B, 0.5% Mo, 4.5% Mn, 10.0% Zn

TABLE 6

Kinetin Stability Data

|     | 0 days | 7 days | 14 days |
|-----|--------|--------|---------|
| #6  | 100.0% | 100.0% | 100.0%  |
| #7  | 100.0% | 100.0% | 100.0%  |
| #8  | 100.0% | 100.0% | 100.0%  |
| #9  | 100.0% | 100.0% | 100.0%  |
| #13 | 100.0% | 96.1%  | 87.6%   |
| #14 | 100.0% | 100.2% | 98.6%   |
| #15 | 100.0% | 95.9%  | 85.5%   |

TABLE 7

IBA Stability Data

|     | 0 days | 7 days | 14 days |
|-----|--------|--------|---------|
| #6  | 100.0% | 99.6%  | 96.6%   |
| #7  | 100.0% | 98.5%  | 95.5%   |
| #8  | 100.0% | 97.2%  | 95.0%   |
| #9  | 100.0% | 103.6% | 103.6%  |
| #13 | 100.0% | 51.0%  | 0.0%    |
| #14 | 100.0% | 97.4%  | 93.0%   |
| #15 | 100.0% | 63.2%  | 52.4%   |

TABLE 8

$GA_3$ Stability Data

|     | 0 days | 7 days | 14 days |
|-----|--------|--------|---------|
| #6  | 100.0% | 100.2% | 97.2%   |
| #7  | 100.0% | 98.9%  | 99.3%   |
| #8  | 100.0% | 100.5% | 101.1%  |
| #9  | 100.0% | 98.3%  | 91.7%   |
| #10 | 100.0% | 98.9%  | 101.3%  |
| #11 | 100.0% | 100.0% | 100.0%  |
| #12 | 100.0% | 100.6% | 99.9%   |
| #13 | 100.0% | 95.4%  | 95.5%   |
| #14 | 100.0% | 92.9%  | 83.3%   |
| #15 | 100.0% | 100.0% | 90.9%   |

The present non-aqueous solution of plant growth regulators (PGRs), such as auxins and gibberellins, in a polar or semi-polar organic solvent have been shown to have increased stability compared to aqueous-based compositions. The increased stability makes the non-aqueous solution more effective in improving the growth and productivity of plants by altering plant architecture as explained above. Significantly, these improvements have been achieved without the use of environmentally hazardous chemicals. The methods to the present invention achieve these improvements by applying naturally occurring or synthetic plant hormones to adjust the phytohormone levels and ratios within the plant tissues to produce the desired results.

Although the present invention has been disclosed in terms of a preferred embodiment, it will be understood that numerous additional modifications and variations could be made thereto without departing from the scope of the invention.

The invention claimed is:
1. A non-aqueous solution comprising:
    a) a plant growth regulator mixture including 0.001 to 1 wt. % at least one auxin, 0.001-0.3 wt. % at least one gibberellin, and 0.001-0.3 wt. % at least one cytokinin;
    b) at least one organic solvent selected from the group consisting of ethanol, n-propanol, iso-propanol, ethyl lactate, 3-hydroxybutyrate (ethyl and propyl esters), glycols, glycerol, polyethylene glycol, polypropylene glycol, propylene carbonate and combinations thereof; and
    c) optionally at least one mineral, optionally at least one surfactant, optionally at least one antifoam, optionally at least one preservative, and optionally combinations thereof, and
    d) less than 5 wt. % water;
    wherein said non-aqueous solution is stable and said at least one organic solvent and said less than 5 wt. % water are the only solvents present in said non-aqueous solution.

2. A non-aqueous solution comprising:
   a) a plant growth regulators mixture including 0.005 to 1 wt. % at least one auxin, 0.005-0.11 wt. % at least one gibberellin, and 0.0015-0.165 wt. % at least one cytokinin;
   b) at least one organic solvent selected from the group consisting of ethanol, n-propanol, iso-propanol, ethyl lactate, 3-hydroxybutyrate (ethyl and propyl esters), glycols, glycerol, polyethylene glycol, polypropylene glycol, propylene carbonate and combinations thereof; and
   c) optionally at least one mineral, optionally at least one surfactant, optionally at least one antifoams, optionally at least one preservative, and optionally combinations thereof, and
   d) less than 5 wt. % water;
   wherein said non-aqueous solution is stable and said at least one organic solvent and said less than 5 wt. % water are the only solvents present in said non-aqueous solution.

3. The non-aqueous solution of claim 1, wherein said organic solvent is polyethylene glycol.

4. The non-aqueous solution of claim 1 wherein said organic solvent is selected from the group consisting of iso-propanol, ethyl lactate, glycerol, polyethylene glycol, polypropylene glycol and combinations thereof.

5. The non-aqueous solution of claim 1, wherein said organic solvent is propylene glycol.

6. The non-aqueous solution of claim 1, wherein said auxin is selected from the group consisting of natural auxins, synthetic auxins, auxin metabolites, auxin conjugates, auxin precursors, auxin derivatives and mixtures thereof.

7. The non-aqueous solution of claim 6, wherein said auxin is selected from the group consisting of indole-3-acetic acid, indole-3-butyric acid (IBA), indole 3-propionic acid, indole-3-butyric acid, phenylacetic acid, naphthalene acetic acid (NAA), 2,4-dichlorophenoxy acetic acid, 4-chloroindole-3-acetic acid, 2,4,5-trichlorophenoxy acetic acid, 2-methyl-4-chlorophenoxy acetic acid, 2,3,6-trichlorobenzoic acid, 2,4,6-trichlorobenzoic acid, 4-amino-3,4,5-trichloropicolinic acid and mixtures thereof.

8. The non-aqueous solution of claim 7, wherein said auxin is indole-3-acetic acid, indole-3-butyric acid (IBA), or mixtures thereof.

9. The non-aqueous solution of claim 2, wherein said cytokinin is selected from the group consisting of zeatin, various forms of zeatin, N6-benzyl adenine, N6-(delta-2-isopentyl) adenine, 1,3-diphenyl urea, thidiazuron, CPPU (forchlorfenuron), kinetin, other chemical formulations with cytokinin activity, and mixtures thereof.

10. The non-aqueous solution of claim 2, wherein said gibberellin is selected from the group consisting of: $GA_i$, $GA_2$, $GA_3$, $GA_4$, $GA_5$, $GA_6$, $GA_7$, $GA_8$, $GA_9$, $GA_{10}$, $GA_{11}$, $GA_{,2}$, $GA_{,3}$, $GA_{,4}$, $GA_{,5}$, $GA_{16}$, $GA_{17}$, $GA_{,8}$, $GA_{19}$, $GA_{20}$, $GA_2i$, $GA_{22}$, $GA_{23}$, $GA_{24}$, $GA_{25}$, $GA_{26}$, $GA_{27}$, $GA_{28}$, $GA_{29}$, $GA_{30}$, $GA_{31}$, $GA_{32}$, $GA_{33}$, $GA_{34}$, $GA_{35}$, $GA_{36}$, $GA_{37}$, $GA_{38}$, $GA_{39}$, $GA_{40}$, $GA_{41}$, $GA_{42}$, $GA_{43}$, $GA_{44}$, $GA_{45}$, $GA_{45}$, $GA_{47}$, $GA_{48}$, $GA_{49}$, $GA_{so}$, $GA_{51}$, $GA_{52}$, $GA_{53}$, $GA_{54}$, $GA_{55}$, $GA_{56}$, $GA_{57}$, $GA_{58}$, $GA_{59}$, $GA_{60}$, $GA_{61}$, $GA_{62}$, $GA_{63}$, $GA_{64}$, $GA_65$, $GA_66$, $GA_{67}$, $GA_{68}$, $GA_{69}$, $GA_{70}$, $GA71$, $GA_{72}$, $GA_{73}$, $GA_{74}$, $GA_{75}$, $GA_{76}$, $GA_{77}$, $GA_{78}$, $GA_{79}$, $GA_{80}$, $GA_8i$, $GA_{82}$, $GA_{83}$, $GA_8$, $GA_{85}$, $GA_{86}$, $GA_{87}$, $GA_{88}$, $GA_{89}$, $GA_90$, $GA_9i$, $GA_{92}$, $GA_{93}$, $GA_{94}$, $GA_{95}$, $GA_{96}$, $GA_{97}$, $GA_{98}$, $GA^\wedge$, GA100, GA101, $GA_{)02}$, $GAio_3$, GA104, GA105, GA106, $GAio_7$, GAios, $GAi_{09}$, GAno, GAm, $GAn_2$, GA113, $GAI\ i_4$, GA115, GA116, GAi i7, GAi is, $GAn_9$, GAno, $GAi_2i$, $GAi_{22}$, $GAi_{23}$, $GAi_{24}$, $GAi_{25}$, GAi26, and mixtures thereof.

11. The non-aqueous solution of claim 2, wherein said auxin, said gibberellin, and said cytokinin retain at least 90% activity after 14 days of Accelerated Storage Stability Testing.

12. The non-aqueous solution of claim 1, wherein said auxin and said at least one additional plant growth regulators retain at least 90% activity after 14 days of Accelerated Storage Stability Testing.

13. The non-aqueous solution of claim 2, wherein the only plant growth regulators are indole-3-butyric acid (IBA), gibberellic acid ($GA_3$), and kinetin.

14. A formulation including said non-aqueous solution of claim 1 and at least one nitrogen-containing fertilizer.

15. The non-aqueous solution of claim 2, wherein the only plant growth regulators are at least one auxin, at least one gibberellin, and at least one cytokinin.

16. The non-aqueous solution of claim 15, wherein said organic solvent is propylene glycol.

17. The non-aqueous solution of claim 2, wherein said organic solvent is propylene glycol.

18. A non-aqueous solution consisting of:
   d) a plant growth regulator mixture including at least one auxin and at least one additional plant growth regulators;
   e) at least one organic solvent selected from the group consisting of ethanol, n-propanol, iso-propanol, ethyl lactate, 3-hydroxybutyrate (ethyl and propyl esters), glycols, glycerol, polyethylene glycol, polypropylene glycol, propylene carbonate and combinations thereof; and
   f) optionally at least one mineral, optionally at least one surfactant, optionally at least one antifoam, optionally at least one preservative, and optionally combinations thereof, and
   d) less than 5 wt. % water;
   wherein said non-aqueous solution is stable and said at least one organic solvent and said less than 5 wt. % water are the only solvents present in said non-aqueous solution.

19. The non-aqueous solution of claim 18, wherein said additional plant growth regulators are selected from the group consisting of cytokinin and gibberellin as the only plant growth regulators.

20. The non-aqueous solution of claim 19, wherein said solution includes 0.005 to 1 wt. % auxin, 0-0.165 wt. % cytokinin, and 0-0.11 wt. % gibberellin as the only plant growth regulators.

* * * * *